US010089752B1

(12) United States Patent
Bronkalla et al.

(10) Patent No.: US 10,089,752 B1
(45) Date of Patent: Oct. 2, 2018

(54) DYNAMIC IMAGE AND IMAGE MARKER TRACKING

(71) Applicant: International Business Machines Corporation, Armonk, NY (US)

(72) Inventors: Mark D. Bronkalla, Waukesha, WI (US); Murray A. Reicher, Rancho Santa Fe, CA (US); James G. Thompson, Escondido, CA (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 15/850,365

(22) Filed: Dec. 21, 2017

Related U.S. Application Data

(63) Continuation of application No. 15/634,127, filed on Jun. 27, 2017.

(51) Int. Cl.
| | |
|---|---|
| *G06K 9/00* | (2006.01) |
| *G06T 7/73* | (2017.01) |
| *G06T 11/60* | (2006.01) |
| *G06T 7/00* | (2017.01) |

(52) U.S. Cl.
CPC ............. *G06T 7/73* (2017.01); *G06T 7/0012* (2013.01); *G06T 11/60* (2013.01); *G06T 2207/30096* (2013.01)

(58) Field of Classification Search
None
See application file for complete search history.

(56) References Cited

U.S. PATENT DOCUMENTS

| | | | | |
|---|---|---|---|---|
| 9,138,175 | B2 | 9/2015 | Ernst et al. | |
| 9,389,084 | B1* | 7/2016 | Chen | G01C 11/06 |
| 2003/0095697 | A1* | 5/2003 | Wood | A61B 6/032 |
| | | | | 382/131 |
| 2006/0093198 | A1* | 5/2006 | Fram | A61B 6/463 |
| | | | | 382/128 |
| 2007/0274585 | A1 | 11/2007 | Zhang et al. | |

(Continued)

OTHER PUBLICATIONS

Abajian, A. C., Levy, M., & Rubin, D. L. (2012). Informatics in radiology: improving clinical work flow through an AIM database: a sample web-based lesion tracking application. Radiographics, 32(5), 1543-1552.*

(Continued)

*Primary Examiner* — Vu Le
*Assistant Examiner* — Samah Beg
(74) *Attorney, Agent, or Firm* — Christopher K. McLane

(57) ABSTRACT

In an approach to tracking markers in one or more images, one or more computer processors identify objects that exist in more than one image from a plurality of images. The one or more computer processors analyze the identified objects for one or more physical characteristics. The one or more computer processors assign a marker to at least one object of the identified objects on at least one image of the more than one image, wherein the marker is annotated based upon the one or more physical characteristics of the object of the identified objects. The one or more computer processors store the more than one images, analysis data, and marker data associated with the identified objects and one or more markers. The one or more computer processors manipulate the one or more images based on a change in the objects across the more than one image.

1 Claim, 6 Drawing Sheets

(56) References Cited

U.S. PATENT DOCUMENTS

| | | |
|---|---|---|
| 2012/0020536 A1 | 1/2012 | Moehrle |
| 2013/0274596 A1 | 10/2013 | Azizian et al. |
| 2016/0048987 A1 | 2/2016 | Sevenster et al. |
| 2016/0232658 A1* | 8/2016 | Syeda-Mahmood ............ G06K 9/00751 |
| 2017/0038951 A1* | 2/2017 | Reicher ............ G06F 19/321 |
| 2018/0055468 A1* | 3/2018 | Reicher ............ A61B 6/468 |
| 2018/0060533 A1* | 3/2018 | Reicher ............ G06F 19/3487 |
| 2018/0060534 A1* | 3/2018 | Reicher ............ G06F 19/3487 |
| 2018/0068438 A1* | 3/2018 | DeVries ............ G06T 7/0012 |
| 2018/0108124 A1* | 4/2018 | Guo ............ G06T 7/0012 |

OTHER PUBLICATIONS

Appendix P, List of IBM Patents or Patent Applications Treated as Related, 2 pages, dated Jan. 17, 2018.

Bauer et al., "Real-Time Range imaging in Health Care: A Survey", Chapter from the book entitled Time-of-Flight and Depth Imaging: Sensors, Algorithms, and Applications, Aug. 2013, ©Springer-Verlag Berlin Heidelberg 2013, DOI: 10.1007/978-3-642-44964-2_11, 26 pages.

Mell et al., "The NIST Definition of Cloud Computing", Recommendations of the National Institute of Standards and Technology, NIST Special Publication 800-145, Computer Security Division Information Technology Laboratory, National Institute of Standards and Technology, Gaithersburg, MD 20899-8930, Sep. 2011, 7 pages.

"Method for Co-Registering Multimodality Imaging Planes", An IP.com Prior Art Database Technical Disclosure, Authors et. al.: Disclosed Anonymously, IP.com No. IPCOM000218792D, IP.com Electronic Publication Date: Jun. 7, 2012; 6 pages.

"Visualization of Medical Images Directly on the Patient Anatomy for C-Arm Navigation and Guidance", An IP.Com Prior Art Database Technical Disclosure, IP.com No. IPCOM000223767D, IP.com Electronic Publication Date: Jul. 4, 2013, 8 pages.

Bronkalla et al., "Dynamic Image and Image Marker Tracking", U.S. Appl. No. 15/634,127, filed Jun. 27, 2017, 52 pages.

\* cited by examiner

DYNAMIC IMAGE AND IMAGE MARKER TRACKING

BACKGROUND OF THE INVENTION

The present invention relates generally to the field of image tracking, and more particularly to the field of tracking and displaying images by applying advanced image tracking to one or more markers.

Image tracking is the process of locating one or more objects over time in one or more images. Imaging tracking has a variety of uses, such as human-computer interaction, security and surveillance, video communication and compression, augmented reality, traffic control, medical imaging and video editing.

Image tracking may use many related images of the same subject matter or taken in quick succession, such as medical images and video capture, respectively. For example, a series of images, such as medical images from an MRI, involve capturing visual representations of a subject over a period of time, such as images of the interior of a body for analysis and clinical representations of the function of one or more tissues, such as organs. Over time, images may be compiled to establish a database of images to act as a self-referential compilation of images allowing a program to detect changes in the images.

SUMMARY

Embodiments of the present invention disclose an apparatus, a method, and a computer program product for processing and displaying images using advanced image tracking. One or more computer processors identify one or more objects that exist in more than one image from a plurality of images. The one or more computer processors analyze the identified one or more objects for one or more physical characteristics. The one or more computer processors assign a marker to at least one object of the identified one or more objects on at least one image of the more than one image, wherein the marker is annotated based upon the one or more physical characteristics of the at least one object of the one or more identified objects. The one or more computer processors store the more than one images, analysis data, and marker data associated with the identified one or more objects and one or more markers. The one or more computer processors manipulate the one or more images based on a change in the one or more objects across the more than one image.

DETAILED DESCRIPTION

Figure 1:
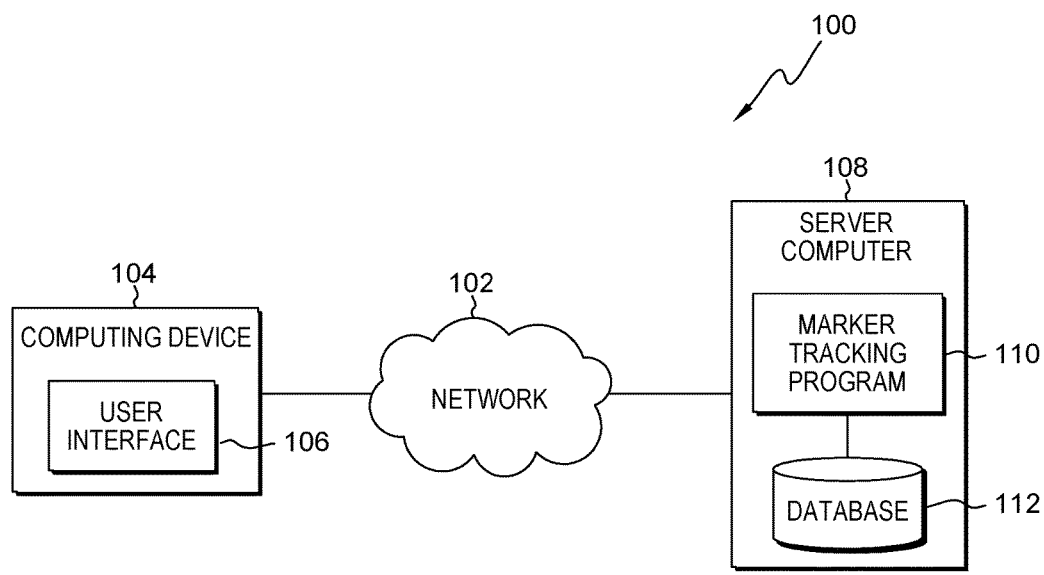
FIG. 1 is a functional block diagram illustrating a distributed data processing environment, in accordance with an embodiment of the present invention.

Present day viewing, assessment, and reporting of multiple related images when tracking and comparing markers in an images requires complex, error-prone, and inefficient manual processes. For example, medical imaging exams are often comprised of many series of images. Such series often include dozens to hundreds of images that are ordered by subject-matter or temporally. Each series may show anatomy from a different vantage point, such as sagittal, coronal, axial, or oblique planes for medical images, may reflect a different image technique (such as different magnetic resonance imaging or computerized tomography methods), or may reflect a different processing method, such as two-dimensional (2D) and three-dimensional (3D) rendering. As result, a series of images may contain hundreds to thousands of images with multiple markers in each of the images in the series of images. Enabling users to quickly finding and sorting the display of images to enable access to one or more markers and to facilitate comparison significantly improves the efficiency, efficacy, and accuracy of image tracking by professionals, such as medical professionals, in assessing changes to one or more markers in a series of images.

In an example, when viewing images, a user (e.g., a radiologists, a cardiologists, other healthcare providers, etc.) the user may wish to mark certain findings for various reasons. In some cases, the images may depict pathology, such as a tumor, an aneurysm, or a fracture. In other instances, the images may represent anatomy that will be tracked over time, such as the normal growth of a structure or movement of a tooth undergoing orthodontic correction. At present, the process of marking images and tracking the progression of user designated markers over time has inefficiencies and redundancies in the navigation back to a series of images with markers for review and comparison. Image tracking can be a time consuming process due to the amount of data that is contained in images. By using object recognition techniques for tracking the time and effort required to accurately track one or more objects over time may be reduced.

In another example, an exam may contain many series of images, each series containing cross-sectional slices arranged in anatomically ordered stacks. A medical imaging exam containing a stack of two dimensional images, such as an MRI, CT, PET/CT, ultrasound, or nuclear imaging scan, various series, may depict the same anatomy in multiple planes. For example, an MRI of the brain may contain images in the axial, sagittal, coronal, and various oblique planes. Also, multiple series in the same plane may show the same anatomy using different techniques that depict tissue contrast differently. For example, variation in window/level settings, variations as to whether intravenous contrast was injected, relative timing of the intravenous contrast injection, and variations in the MRI pulse sequence during the image acquisition each depict tissue contrast differently. In other instances, a stack of images may be processed using advanced visualization software, such that the user may interactively display images derived from the volume of data as multi-planar reconstructed images or as three-dimensional (3D) volume-rendered images. Such 3D images may be depicted in color or monochrome using techniques such as surface shading and color transformations in order to optimize the appearance and vantage point when viewing certain tissues. A user may employ software to rotate the display of planar or 3D images or dynamically create multi-planar reformatted images.

Despite the ability to designate one or more images as key images, a user who wishes to view and compare marked findings faces significant drawbacks when seeking to efficiently and effectively display one or more marked findings. A user must locate and display a finding or many findings on one or more images of the current image series and appropriate comparison image series, with each image series potentially including thousands of images from which to select. Simply stated, navigation to marked findings or synchronous display of a particular marked finding on the current image and prior image series poses significant challenges with the current limitations in imaging technology.

By creating relational databases highlighting the connections between various markers for one or more image series, such as images from medical exams for a patient and lesion data, in an efficient manner, multiple users can better grasp how one or more markers indicating particular subject matter in the image series relate to one another, such as multiple health care professionals attempting to identify how particular physiological afflictions interact with each other. For example, a healthcare provider can focus more heavily on finding a solution to a medical issue rather than deciphering the basic connections between one or more lesions to identify the medical issue. Implementation of embodiments of the invention may take a variety of forms, and exemplary implementation details are discussed subsequently with reference to the Figures.

FIG. 1 is a functional block diagram illustrating a distributed data processing environment, generally designated 100, in accordance with one embodiment of the present invention. The term "distributed" as used in this specification describes a computer system that includes multiple, physically distinct devices that operate together as a single computer system. FIG. 1 provides only an illustration of one implementation and does not imply any limitations with regard to the environments in which different embodiments may be implemented. Many modifications to the depicted environment may be made by those skilled in the art without departing from the scope of the invention as recited by the claims.

Distributed data processing environment 100 includes computing device 104 and server computer 108 interconnected over network 102. Network 102 can be, for example, a telecommunications network, a local area network (LAN), a wide area network (WAN), such as the Internet, or a combination of the three, and can include wired, wireless, or fiber optic connections. Network 102 can include one or more wired and/or wireless networks that are capable of receiving and transmitting data, voice, and/or video signals, including multimedia signals that include voice, data, and video information. In general, network 102 can be any combination of connections and protocols that will support communications between computing device 104 and server computer 108, and other computing devices (not shown) within distributed data processing environment 100.

Computing device 104 can be a laptop computer, a tablet computer, a smart phone, or any programmable electronic computing device capable of communicating with various components and devices within distributed data processing environment 100, via network 102. In general, computing device 104 represents any programmable electronic computing device or combination of programmable electronic computing devices capable of executing machine readable program instructions, manipulating executable machine readable instructions, and communicating with server computer 108 and other computing devices (not shown) within distributed data processing environment 100 via a network, such as network 102. Computing device 104 includes an instance of user interface 106. Computing device 104 and user interface 106 allow a user to send one or more images to marker tracking program 110 and receive one or more images and marker data from marker tracking program 110.

User interface 106 provides an interface to marker tracking program 110 on server computer 108 for a user of computing device 104. In one embodiment, user interface 106 may be a graphical user interface (GUI) or a web user interface (WUI) and can display text, documents, web browser windows, user options, application interfaces, and instructions for operation, and include the information (such as graphic, text, and sound) that a program presents to a user and the control sequences the user employs to control the program. In another embodiment, user interface 106 may also be mobile application software that provides an interface between a user of computing device 104 and server computer 108. Mobile application software, or an "app," is a computer program designed to run on smart phones, tablet computers and other mobile devices. In an embodiment, user interface 106 enables the user of computing device 104 to upload one or more images and one or more markers associated with the one or more images to marker tracking program 110 and access one or more images and marker data associated with the one or more markers on computing device 104.

Server computer 108 can be a standalone computing device, a management server, a web server, a mobile computing device, or any other electronic device or computing system capable of receiving, sending, and processing data. In other embodiments, server computer 108 can represent a server computing system utilizing multiple computers as a server system, such as in a cloud computing environment. In another embodiment, server computer 108 can be a laptop computer, a tablet computer, a netbook computer, a personal computer (PC), a desktop computer, a personal digital assistant (PDA), a smart phone, or any other programmable electronic device capable of communicating with computing device 104 and other computing devices (not shown) within distributed data processing environment 100 via network 102. In another embodiment, server computer 108 represents a computing system utilizing clustered computers and components (e.g., database server computers, application server computers, etc.) that act as a single pool of seamless resources when accessed within distributed data processing environment 100. Server computer 108 includes marker tracking program 110 and database 112. Server computer 108 may include internal and external hardware components, as depicted and described in further detail with respect to FIG. 4. In other embodiments, server computer 108 and computing device may be implemented in a cloud-based environment, as depicted and described in further details with respects to FIG. 5 and FIG. 6.

Marker tracking program 110 resides on server computer 108 and initiates when marker tracking program 110 receives data, such as an image, from a user. For example, a user may upload one or more images through a user interface, such as user interface 106, into database 112 in advance for later retrieval by marker tracking program 110.

In a first function, marker tracking program 110 identifies one or more subjects in one or more images. Marker tracking program 110 analyzes one or more identified subjects. Marker tracking program 110 assigns one or more markers associated with the one or more identified subjects. Markers may be any representation indicating the presence of one or more identified subjects. For example, a marker may be an arrow pointing to a portion of an image deemed important by a user. Marker tracking program 110 stores identified subject analysis data associated with the one or more markers. Marker tracking program 110 displays the one or more markers and identified subject analysis data.

In a second function of marker tracking program 110, marker tracking program 110 receives one or more requests for one or more images and one or more identified subject analyses associated with the one or more markers associated with one or more identified subjects. Marker tracking program 110 compiles one or more previously stored images and previously stored subject analyses associated with the one or more markers. Marker tracking program 110 determines whether a relationship exists between the identified subject and the one or more previously stored images and previously stored subject analyses. In an embodiment, marker tracking program 110 analyzes subjects related to a medical image including an annotation marking a particular finding or portion of the image deemed important by a user. An annotation may signify a classification of an object in an image. For example, marker tracking program 110 may assign a tumor identified by the physical characteristics of the tumor an annotation represented by a triangle-shaped marker. The triangle-shaped annotation may signify that the object belongs in a class associated with cancerous growths. Such an annotation may be designed to allow the user to infer whether the marking refers to one or more pixels within the displayed image versus one or more pixels from another image depicting another anatomical location or point-in-time in the same series of images. Responsive to determining that a change between the identified subject and the one or more previously stored images and the one or more previously stored subject analyses does not exist, marker tracking program 110 creates a subject analysis report. Responsive to determining that a relationship between the identified subject associated with the one or more markers and the one or more previously stored images and previously stored subject analyses exists, marker tracking program 110 updates subject analysis data. After storing the subject analysis data or following a determination that a relationship between the identified marker and the one or more previously stored images and the one or more previously stored marker analyses does not exist, marker tracking program 110 creates one or more subject analysis reports. Lastly, marker tracking program 110 sends one or more subject analysis reports. Marker tracking program 110 is depicted and described in further detail with respect to FIGS. 2 and 3.

Database 112 is a repository for data used and stored by marker tracking program 110. In the depicted embodiment, database 112 resides on server computer 108. In another embodiment, database 112 may reside elsewhere within distributed data processing environment 100 provided marker tracking program 110 has access to database 112. A database is an organized collection of data. Database 112 can be implemented with any type of storage device capable of storing data and configuration files that can be accessed and utilized by server computer 108, such as a database server, a hard disk drive, or a flash memory. Database 112 stores required access request parameters, user access permissions, and data corresponding to user access permissions of a computing device, such as computing device 104. Database 112 also stores registration and configuration data inputted by a user of computing device 104 via user interface 106 for the purpose of providing marker tracking program 110 the means to identify a user and the associated user access permissions. Database 112 may also store subject analysis data and subject images. Database 112 may also store data associated with the historical access request parameters, user access permissions, and data corresponding to user access permissions of computing device 104.

Figure 2:
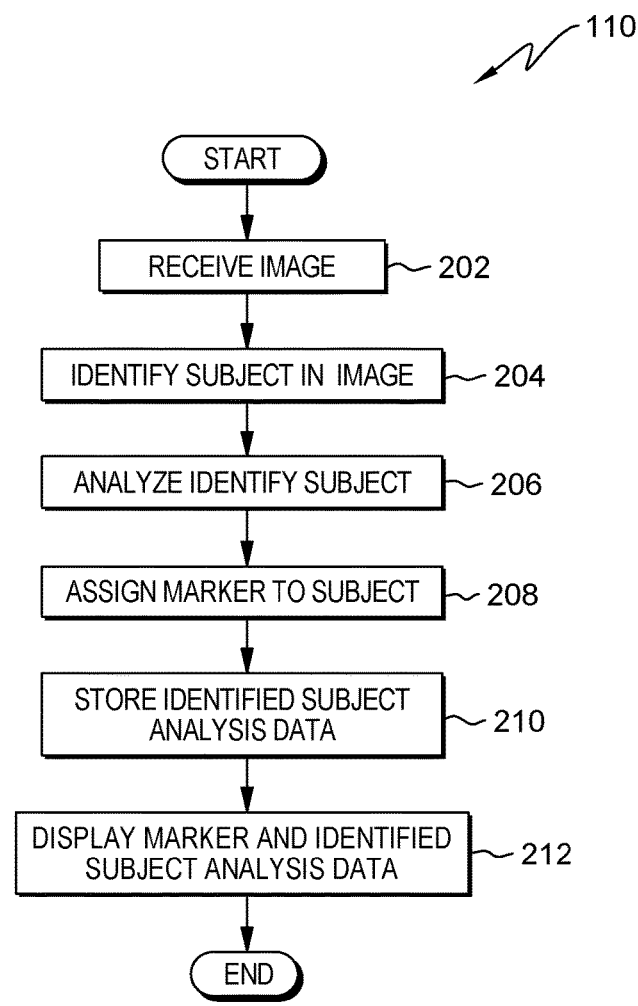
FIG. 2 is a flowchart depicting the operational steps of a first function of a marker tracking program, on a server computer within the distributed data processing environment of FIG. 1, for analyzing one or more lesions, in accordance with an embodiment of the present invention.

FIG. 2 is a flowchart depicting operational steps of a first function of marker tracking program 110, on server computer 108 within distributed data processing environment 100 of FIG. 1, for analyzing one or more marker associated with subject matter in one or more images, in accordance with an embodiment of the present invention. The first function of marker tracking program 110 starts when marker tracking program 110 receives one or more images.

Marker tracking program 110 receives data, such as an image, from a user (step 202). A user may upload one or more images into database 112 in advance for later retrieval by marker tracking program 110 via a user interface, such as user interface 106. In one embodiment, marker tracking program 110 may receive a set of images taken directly from a medical imaging exam. For example, marker tracking program 110 may receive a set of images directly from a magnetic resonance imaging (MRI) brain scan using a gadolinium contrast agent. In another example, marker tracking program 110 may directly receive a set of images from a radiographic scan of vital organs and vasculature of a patient using an iodinated contrast. In yet another example, marker tracking program 110 may directly receive a set of x-ray images taken from a computerized tomography (CT) scan in various angles to create cross-sectional images representing slices of blood vessels, bones, and soft tissues in the body of a patient.

In another embodiment, marker tracking program 110 may receive a set of images taken from a series of images, such as multiple images of the same subject over time or multiple images taken from a stationary video camera. For example, a series of images taken of an arctic ice shelf over time may be received for further analysis of one or more subjects in the image over time, such as tracking the change of ice over time. In another example, one or more series of images from a still video taken of a golfer over time may be received by marker tracking program 110 for an analysis of particular points of a swing to automatically assess changes in the form of the golfer over time.

In another embodiment, marker tracking program 110 may receive one or more sets of lesion images marked by one or more physicians. For example, marker tracking program 110 may receive a set of MRI images and a set of CT scan images marked by a physician for a particular organ in a patient. In another example, marker tracking program 110 may receive a set of MRI images and a set of CT scan images marked by two different physicians for a particular organ in a patient over a network, such as network 102, to be stored in database 112 in a cloud-computing environment.

Marker tracking program 110 identifies one or more subjects in one or more images (step 204). Marker tracking program 110 may identify the one or more subjects in one or more images using methods known in the art. For example, marker tracking program 110 may use statistical analyses and supervised learning classifiers to identify one or more subjects in one or more images. Marker tracking program 110 may also identify the one or more subject using any characteristics or combination of characteristics that make the one or more subjects unique compared to the surroundings of the one or more subjects. Subjects may include any subject matter, such as points of interest to a user. In an example, a user might deem lesions to be subject matter of interest. A lesion may be any specified region in an organ or tissue that contains tissue that deviates from non-afflicted tissue. Lesions may be detected using any identifiable characteristics, such as size, shape, color, and contrast based on intravenous contrast injections.

In an embodiment, marker tracking program 110 may identify a lesion by detecting the altered pixel intensity, such as the intensity of coloration, of a tissue after a contrast injection. For example, a physician may inject an intravenous iodinated contrast in a patient to produce a contrast between non-enhancing tissue, such as tissue that does not take-up an iodinated contrast agent, and enhancing tissue, such as tissue that does take-up an iodinated contrast agent, indicating the presence of a lesion, vascular structure, or a particular organ. Thus, marker tracking program 110 may detect the altered appearance of an abnormality located in the body of a patient.

In another example, a physician may inject air or contrast material in a patient through the rectal cavity to detect lesions in the gastrointestinal system. As a result, marker tracking program 110 may detect the altered appearance of one or more colorectal polyps present in the large intestine of a patient. In another example, a physician may inject an intravenous gadolinium contrast agent to identify areas of active inflammation in the brain by detecting the movement of the gadolinium contrast agent stored the blood brain barrier. Thus, marker tracking program 110 may identify areas where active inflammation is present in the vital organs of a patient.

In another embodiment, marker tracking program 110 may identify a subject without the use of any agents. For example, marker tracking program 110 may receive one or more lesion images from a T1-weighted MRI brain scan without the use of a gadolinium contrast agent to identify the areas of active inflammation in the brain and identify areas of nerve damage by identifying darkened areas (e.g., hypointensities) that indicate areas of permanent nerve damage. However, marker tracking program 110 may identify one or more subjects from any known imaging techniques using any technique known in the art.

In yet another embodiment, marker tracking program 110 may identify one or more subjects in an image series. For example, marker tracking program 110 may identify one or more subjects associated with the stance and movement of a tennis player during a swing, such as the location of the elbow, the width of the feet, and the rotation angle of the shoulders. Marker tracking program 110 may identify one or more subjects in an image series based on characteristics particular to an object. For example, marker tracking program 110 may identify a nose on a face by the combination of physical characteristics particular to a nose, such as nostrils, a nose bridge, the shape of the nostrils formed by the nasal cartilages, the length of the nose, the width of the nose, and the placement of the nose on the human face.

Marker tracking program 110 analyzes one or more identified subjects (step 206). Marker tracking program 110 may analyze previously identified subjects and compare the previously identified subjects to the current state of the subject. Subjects may include any type of object that can be captured by an imaging device. For example, marker tracking program 110 may analyze an identified subject based on characteristics unique to the identified subject. Marker tracking program 110 may analyze preset characteristics, such as characteristics designated by a user, characteristics commonly associated with the identified subject, or characteristics designated by an artificial intelligence-based program using one or more analytical techniques, such as statistical analyses or supervised learning classifiers. For example, marker tracking program 110 may analyze the unique coloration, density, and shape unique to a tumor in an image to compare with an image taken of the tumor at a later time. Marker tracking program 110 may analyze the one or more identified subjects using any analytical technique known in the art and analyze any subject based on any characteristics. For example, marker tracking program 110 may use analytical techniques, such as edge tracking, gradient tracking, greyscale tracking, and outline tracking. For example, marker tracking program 110 may analyze the size, the shape, the color, the textural characteristics, and any combination thereof of any subject in any image. Marker tracking program 110 may analyze one or more identified subjects which are associated with one or more markers assigned by a user or marker tracking program 110. The method a user may employ to assign a marker to a subject is described in further detail in step 208. Markers may be updated by marker tracking program 110 or assigned to a newly identified subject. As such, marker tracking program may analyze previously identified subject associated with existing markers or newly identified subjects which may be assigned a marker at an earlier or later step in the present invention.

In one example, marker tracking program 110 may compare previously stored lesion images and previously stored lesion analyses to analyze the change in a particular lesion. For example, marker tracking program 110 may compare the size of a lesion in one or more previous lesion images of a patient over time to the size of a lesion in a current lesion image. Based on a determination that the size of the lesion increased by analyzing the percentage of the image the lesion occupies in a set area currently versus the previously stored lesion images, marker tracking program 110 may determine that the lesion has grown.

Alternatively, based on a determination that the size of the lesion decreased by analyzing the percentage of the image the lesion occupies in a set area currently versus the previously stored lesion images, marker tracking program 110 may determine that the lesion has reduced in size. In yet another example, marker tracking program 110 may compare the location of a bodily structure, such as a bone or a tumor, in a current lesion image to previous lesion images for a patient over time to determine the movement of the bodily structure in the body of the patient.

In another embodiment, marker tracking program 110 may compare the size of a lesion in a current lesion image to control lesion images to determine how much the lesion of a patient deviates from the norm to determine the severity of an injury. For example, marker tracking program 110 may compare a hemorrhage in the brain to lesion images of normal tissue derived from a database of existing patients to determine that a patient is suffering from internal bleeding.

In yet another embodiment, marker tracking program 110 may compare markers indicating points of interest in a golf swing, such as the location of the head, the rotational angle of the shoulder, and the width of the feet, in multiple series of images to track how the swing changed over time. For example, marker tracking program 110 may compare the subjects associated with the one or more markers to stored subject analysis data to determine whether the swing has changed to fix problems identified in stored analyses of the golf swing.

Marker tracking program 110 assigns one or more markers (step 208). A marker may be a simple graphic icon indicating the location of a subject in one or more image. For example, a marker may indicate the presence of a lesion. A marker may be an interactive marker that allows a user to trigger a machine-readable or executable program. For example, a marker may present prior lesion analyses in a graphic user interface when a user uses a cursor to select on the lesion marker displayed on the screen. As such, a marker may act as a navigation tool. A marker may also directly convey information based on annotations in the marker indicating one or more physical characteristics of one or more objects using various mediums, such as a symbol, a color, alphanumeric text, and a size of the marker.

In one embodiment, marker tracking program 110 may display one or more types of markers that enable the user to infer whether the marker marks a lesion in the currently displayed image versus marking an image located elsewhere in the same displayed image series. For example, the marker may enable the user to indicate the placement of a subject in a stack of images, such as indicating whether the marker exists in the current image or other images in an image series, based on the appearance of the marker, such as whether the marker is sharp versus blurred, the color of the marker, the size of the marker, the opacity of the lesion marker, or an annotation that is displayed in association with the marker. In one embodiment, an annotation may appear in response to a user action such as a user selecting a marker with a cursor, an audio command, or hovering a cursor on a graphic user interface over the marker.

In another embodiment, the appearance of the marker may show an indication of the relative location of the marked subject in relation to the currently displayed subject image. For example, a marker may be fainter, fuzzier, smaller, darker in color/shade, or more transparent to indicate that the finding is more subject images away from the currently displayed subject image than a marker that is more intense, sharper, larger, or lighter. As such, the user may gain an understanding of the relative distance to a marked subject or the order in which marked subjects will be encountered while paging through an image series, such as a stack of lesion images representing slices of a 3D object, which allows a user to intuitively derive information from the marker itself. In another example, a marker may have a different appearance depending on the type of subject in the subject image. For example, a subject marker, such as a lesion marker, that is square shaped may indicate a contusion while a subject marker that is circular may indicate a tumor.

In yet another embodiment, marker tracking program 110 may display multiple interactive markers associated with a stack of subject images which may make the subject image associated with a selected marker visible in the forefront when selected by a user. For example, marker tracking program 110 may receive an input from a user selecting a particular lesion marker in the brain associated with a second tumor. In response, marker tracking program 110 may bring the clearest image of the second tumor to the forefront of the stack or automatically page through the stack of subject images to display the marked subject image.

In yet another embodiment, marker tracking program 110 may display multiple interactive subject markers associated with a stack of subject images which may make the subject image associated with the selected marker display on a graphical user interface when selected by a user. For example, if a user selects a subject marker, such as a lesion marker, indicating the fifteenth image of a twenty slide image set from an MRI scan then marker tracking program 110 may move to the fifteenth image upon selection of the marker associated with the fifteenth image. In this example, the remaining subject images in the set of subject images would not be visible once a user selects a specific subject image.

In yet another embodiment, marker tracking program 110 may allow a user to narrow the number of markers displayed by controlling one or more variables or user preferences associated with the markers. For example, a subject image series, such as a stack of lesion images from a CT scan, may extend through a large segment of the human body and the number of markers displayed may cause problems in identifying and selecting particular markers associated with one or more subjects. To remedy this issue, marker tracking program 110 may allow a user to create and control variables or user preferences that determine the limits for how far a subject can be from the current subject image in a 3D space for the system to display a marker. The variables may also include a type of imaging device, a type of imaging, a modality, a body part, a user location, a site preference, and any combination thereof. The variables are not limited to the embodiments discussed herein and may include any variables known in the art.

In another embodiment, marker tracking program 110 may automatically control the variables associated with one or more markers by machine learning algorithms, such as an artificial intelligence system that tracks and determines features related to the activities of a user. For example, a machine learning algorithm, such as a supervised learning classifier, executed by marker tracking program 110 may make a determination that a radiologist historically looks at related to a primary subject within five centimeters of the primary subject, such as a tumor, to scan for affected surrounding tissues. As such, marker tracking program 110 may only display markers within a five centimeter radius from a marker associated with the subject.

In yet another embodiment, marker tracking program 110 may assign one or more positional markers indicating the position of one or more subject features. For example, marker tracking program 110 may assign positional markers to the hips, the shoulders, the feet, and the elbows of a golfer after analyzing one or more images of a golf swing. Marker tracking program 110 assigns one or more positional markers indicating the position of one or more subject features in order to enable marker tracking program 110 to dynamically track subject features for subject analysis, such as changes in movement, size, and shape.

Marker tracking program 110 stores identified subject analysis data associated with the one or more markers (step 210). Subject analysis data may include analysis data about any subject, such as objects in an image and other potential points of interest to a user. Subjects as used herein may be synonymously used with objects. In an example, subject analysis data may include any information associated with a lesion in one or more images containing one or more lesions and associated with one or more markers. For example, marker tracking program 110 may store identified subject analysis data associated with a marker for a tumor, such as a current size of the tumor, a percentage of growth since the last imaging of the tumor, a type of tumor, a tracked movement of the tumor in the body, one or more organs affected or in danger of being affected by the tumor, and the relationships between the identified subject associated with a marker and other existing subject associated with one or more markers in the body of a patient. In one embodiment, marker tracking program 110 may store identified subject analysis data on a database, such as database 112. In another embodiment, marker tracking program 110 may store identified subject analysis data in a cloud-based environment over network 102 to be accessed by authorized entities, such as physicians and health organizations.

Marker tracking program 110 displays the one or more markers and identified subject analysis data (step 212). In one embodiment, marker tracking program 110 may display one or more markers and identified subject analysis data, such as subject analysis data of a lesion, in a web-user interface. For example, marker tracking program 110 may display the one or more markers and identified subject analysis data on an internal website for healthcare providers in a hospital network. In another embodiment, marker tracking program 110 may display one or more markers and identified subject analysis data in a graphic user interface. For example, marker tracking program 110 may display the one or more markers and identified subject analysis data in a program downloaded by one or more physicians on a computer, tablet computer, and smartphone. The aforementioned example may also be implemented in a cloud-based environment which allows multiple users to access a seamless and interconnected pool of data. In an alternative embodiment, marker tracking program 110 may not display the one or more markers and identified subject analysis data until a user executes machine-readable program instructions to display the one or more markers and identified analysis data associated (e.g., one or more lesions). For example, marker tracking program 110 may assign one or more markers as marker tracking program 110 receives identified subject analysis data but only display the information once a user, such as a physician, requests the identified subject analysis data.

Figure 3:
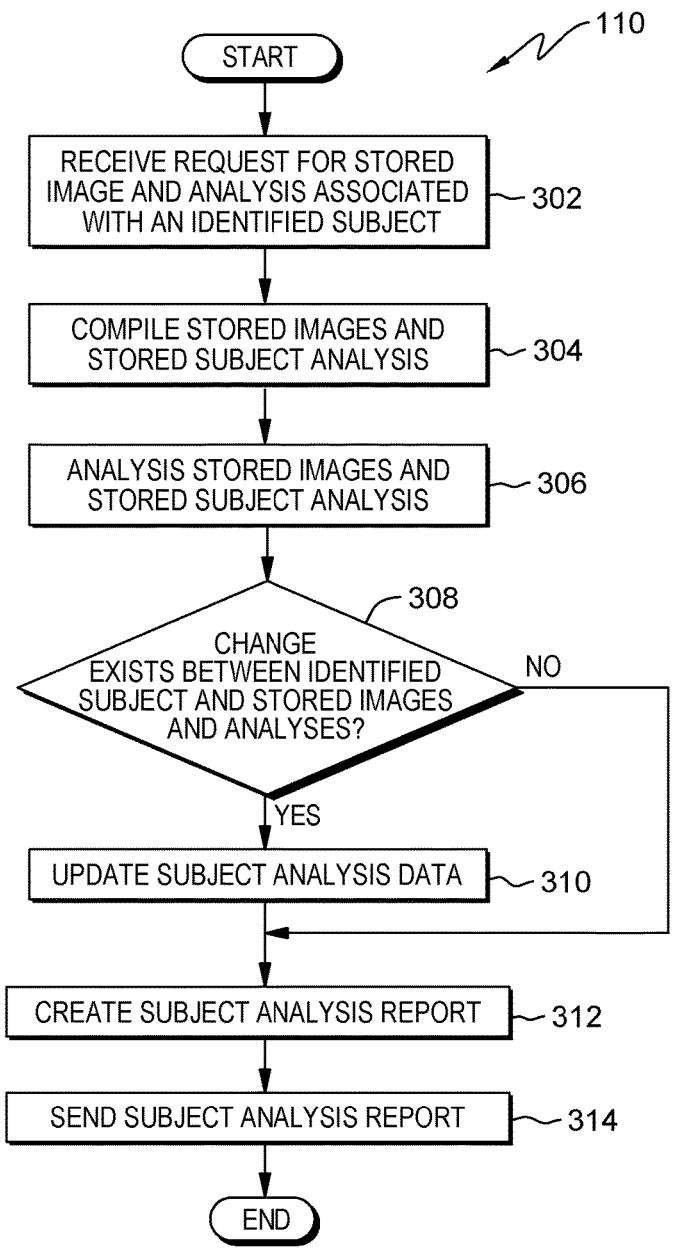
FIG. 3 is a flowchart depicting operational steps of a second function of a marker tracking program, on a server computer within the distributed data processing environment of FIG. 1, for determining relationships between one or more lesions and creating a lesion analysis report, in accordance with an embodiment of the present invention.

FIG. 3 is a flowchart depicting operational steps of a second function of marker tracking program 110, on server computer 108 within distributed data processing environment 100 of FIG. 1, for determining relationships between one or more subjects and creating a subject analysis report, in accordance with an embodiment of the present invention. The second function of marker tracking program 110 starts when marker tracking program 110 receives a request for one or more previously stored images and one or more previously stored subject analyses associated with an identified subject.

Marker tracking program 110 receives one or more requests for one or more subject images and one or more subject analyses associated with the identified subject (step 302). In one embodiment, marker tracking program 110 may receive one or more requests for one or more subject images and one or more subject analyses associated with the identified subject from one or more users. For example, a team of medical professionals, such as a nurse practitioner, an anesthesiologist, and a surgeon, responsible for a surgery may request images of a tumor and associated tumor analyses before the procedure. In another embodiment, marker tracking program 110 may receive one or more requests for one or more types of images and one or more types of subject analyses associated with the identified subject. For example, a physician may request one or more lesion images and one or more lesion analyses from an MRI and a CT scan to get a better understanding of a lesion based on various types of imaging.

Marker tracking program 110 compiles one or more previously stored subject images and the one or more previously stored subject analyses (step 304). In one embodiment, marker tracking program 110 compiles one or more previously stored subject images and the one or more previously stored subject analyses from a database, such as database 112. For example, marker tracking program 110 may compile one or more previously stored lesion images and one or more stored lesion analyses of a tumor in a patient from an internal database, such as a solid state drive. In another embodiment, marker tracking program 110 may compile one or more previously stored subject images and the one or more previously stored subject analyses from a cloud-computing network by accessing multiple databases connected over a network, such as network 102. In an alternative embodiment, marker tracking program 110 may not compile one or more previously stored images and the one or more previously stored subject analyses if the image received from a user is a first set of subject images and a first set of subject analyses. However, marker tracking program 110 may compile data associated with one or more subjects using any method known in the art.

Marker tracking program 110 analyzes the one or more previously stored images and the one or more previously stored subject analyses (step 306). Marker tracking program 110 may analyze any characteristics associated with a subject in one or more subject images and associated with one or more markers. In one embodiment, marker tracking program 110 may analyze one or more subjects for one or more changes by retrieving previously stored subject analyses associated with a marker and comparing the previously stored subject analyses to a current subject image. For example, marker tracking program 110 may determine the growth of a tumor by comparing how much space the tumor occupies in the current image to how much space the tumor occupied in stored subject images associated with a patient.

In another embodiment, marker tracking program 110 may analyze one or more subjects for growth by retrieving previously stored subject analyses associated with a marker and comparing previously stored subject analyses to a current subject image. For example, marker tracking program 110 may determine the growth of a tumor by comparing how much space the tumor occupies in the current subject image to how much space the tumor occupied in stored subject images associated with a patient.

In yet another embodiment, marker tracking program 110 may analyze one or more subjects for a percentage of growth by retrieving previously stored subject analyses associated with a marker and comparing previously stored subject analyses to a current subject image. For example, marker tracking program 110 may determine the percentage of growth of a tumor by comparing how much space the tumor occupies in the current subject image divided by the overall area of the current subject image to how much space the tumor occupied in stored subject images divided by the respective overall areas of the previously stored subject images associated with a patient.

In yet another embodiment, marker tracking program 110 compares and analyzes one or more subject images automatically and subsequently manipulates one or more images using one or more image techniques. Marker tracking program 110 may analyze one or more objects in more than one image based on the shared one or more unique physical traits of the one or more objects and the shared one or more unique physical traits of the area surrounding the one or more objects in the more than one image to establish a first position of the objects in each respective image. Following the establishment of a first position of the objects, marker tracking program 110 may adjust the positional characteristics, such as the scaling, the centering, and the obliquity, of each object in one or more images based on distinct traits of each image of an object and each image of the area surrounding the object. For example, marker tracking program 110 may bring the subject images to the same scaling and centering around one or more points of concern, such as a tumor that has grown substantially, to further facilitate comparison of the one or more subject images using the above described marking system. Scaling is defined herein as presentation of images so that distances in the subject of the image are displayed in the comparative images at the same scale. For example, a one centimeter marker in one subject image will be displayed the same size as a one centimeter marker in another related subject image. Centering around the point of concern is the positioning within a display area so that a point of concern is in the same relative location compared to the overall frame around the subject image. For example, marker tracking program 110 may enable a user to superimpose one subject image over a second related subject image or quickly switch between the display of one subject image and a second related subject image so that the two related subject images will be aligned as closely to each other based on image traits, such as positioning, one or more points of concern, and one-to-one scaling.

In yet another embodiment, marker tracking program 110 may align the rotation of one or more subject images. In yet another embodiment, marker tracking program 110 may adjust the rotational alignment of one or more subject images in response to a user action. For example, a user selecting a marker may cause marker tracking program 110 to align and scale comparative subject images relative to the selected marker when a subject image has more than one marker. In a related example, a user selecting a second marker may cause marker tracking program 110 to align and scale comparative subject images relative to the second marker when a subject image has more than one marker.

In yet another embodiment, marker tracking program 110 may automatically reconstruct one or more subject images so that a first subject image and a second subject image displaying a subject are also matched in obliquity. For example, marker tracking program 110 may match the widest portion of a lesion in multiple sets of lesion images representing the 3D structure of a lesion in a multitude of slices, either automatically or by a user action. In one example, marker tracking program 110 may reconstruct one or more lesion images in response to the user clicking on a particular lesion marker. In another example, marker tracking program 110 may automatically select an obliquity that shows a long axis of a marked lesion based on analysis of the geometric volume of the marked lesion.

In yet another embodiment, marker tracking program 110 may, in response to a default configuration, rule, or user action, such as a user selecting a marker, create a chronologically ordered stack of related subject images containing a selected subject image from the selected subject image and one or more comparison subject images that best depict the subject from one or more imaging technologies. For example, the user may quickly switch (e.g., shuffling, flickering, paging, and etc.) to and from one or more lesion images an image series to compare the change of a subject over time.

In yet another embodiment, marker tracking program 110 may optimize the comparison and analysis of one or more subject images from one or more imaging techniques by adjusting the images to match as closely as possible in relation to a selected subject with regard to scaling, centering, rotation, window/level, obliquity, color, opacity, transformation, and any other characteristics. In one example, marker tracking program 110 may optimize the comparison and analysis of one or more lesion images from one or more imaging techniques by adjusting the subject images, such as slices of a CT scan, to match as closely as possible in relation to a selected lesion with regard to scaling, centering, rotation, window/level, obliquity, color, opacity, transformation, and any other characteristics in response to a user action. In another example, marker tracking program 110 may optimize the comparison and analysis of one or more lesion images from one or more imaging techniques by adjusting the subject images, such as slices of a MRI scan, to match as closely as possible in relation to a selected lesion with regard to scaling, centering, rotation, window/level, obliquity, color, opacity, transformation, and any other characteristics automatically based on one or more algorithms, such as machine learning algorithms. Machine learning algorithms may include, but are not limited to, statistical analyses, supervised learning classifiers, and time-series models.

In a related example, marker tracking program 110 may use the type of subject, the one or more imaging techniques associated with one or more imaging modalities, one or more organs, one or more patients, one or more suspected problems, and any combination thereof to optimize the comparison of one or more subject images.

In yet another embodiment, marker tracking program 110 may enable a user to select one or more marked subjects and perform a user action to trigger the display of one or more subject images from one set of subject images from an image series that show the one or more marked subjects. In yet another embodiment, marker tracking program 110 may automatically select one or more marked subjects and display one or more subject images from one set of subject images from an image series that show the one or more marked subjects. In yet another embodiment, marker tracking program 110 may enable a user to perform a user action causing marker tracking program 110 to display one or more selected markers and show matching subject images associated with the one or more selected markers from other image series. In yet another embodiment, marker tracking program 110 may sort one or more subject images for comparison and analysis by the particular subject, or any combination thereof.

In yet another embodiment, marker tracking program 110 may analyze a subject image for any characteristics known in the art that are associated with one or more subjects. For example, marker tracking program 110 may use a machine learning algorithm to analyze a lesion image for any characteristics associated with the one or more lesions, such as a supervised learning classifier, to determine a type of tumor, a change in pixel intensity, a pixel homogeneity, a contrast enhancement, movement of a lesion or adjacent structures, and any combination thereof. Alternatively, marker tracking program 110 may also use one or more machine learning algorithms to analyze one or more stored subject images without a newly received subject image.

In yet another embodiment, marker tracking program 110 may analyze a subject image for areas of further research and analysis. For example, marker tracking program 110 may analyze a lesion image for additional health afflictions that may be caused by the lesion and suggest medical procedures to aid in further analysis. Illustrating the aforementioned more specifically, marker tracking program 110 may determine a high likelihood that a tumor may be pressing on the pituitary gland of a patient which is causing hormonal imbalances in the patient from one set of lesion images and previously stored lesion images taken from a particular angle. As such, marker tracking program 110 may suggest an MRI brain scan using a contrast agent from a different angle to aid in determining whether the hormonal imbalance of the patient may be a result of the predicted cause.

Marker tracking program 110 determines whether a change exists between the identified subject and the one or more previously stored subject images and previously stored subject analyses (decision block 308). In one embodiment, marker tracking program 110 determines whether a change exists between an identified subject, such as a lesion, and the one or more previously stored subject images, such as lesion images. In another embodiment, marker tracking program 110 determine whether a change exists between the identified subject and the one or more previously stored subject images based on a threshold. For example, marker tracking program 110 may be manually configured to only register changes in size of a tumor on a current lesion image as a substantive change if the change in size is greater than two percent. In another example, marker tracking program 110 may be configured through machine learning algorithms to only register changes in size of a tumor on a current lesion image as a substantive change if the change in size is greater than two percent. In an alternative embodiment, marker tracking program 110 may not determine whether a change exists between the identified subject and the one or more previously stored subject images and previously stored subject analyses. In another alternative embodiment, marker tracking program 110 may determine if a change exists between multiple stored subject analyses without comparing the multiple subject lesion analyses to a currently identified subject. However, marker tracking program 110 may determine whether a change exists between the identified subject and the one or more previously stored subject images and previously stored subject analyses in any manner known in the art.

Responsive to determining that a change between the identified subject and the one or more previously stored subject images and the one or more previously stored subject analyses does not exist ("No" branch, decision block 308), marker tracking program 110 creates a subject analysis report (step 312). A subject analysis report may include any relevant information pertaining to the one or more subjects associated with one or more markers represented in the report. In one embodiment, a subject analysis report may include the changes to the subject over time. For example, marker tracking program 110 may include data on the movement and growth of a subject, such as a tumor, in the body of a patient in the subject analysis report. In another example, marker tracking program 110 may include data on the shrinkage of a tumor in the body of a patient in a subject analysis report. In another embodiment, a subject analysis report may include suggested actions based on findings made by marker tracking program 110. For example, marker tracking program 110 may apply a machine learning algorithm, such as a supervised learning classifier, to suggest a medical exam with the highest probability of identifying one or more medical issues in a patient. Based on the information, marker tracking program 110 may include suggested medical exams in the subject analysis report to be displayed in user interface 106, such as a graphic user interface, with interactive markers.

Responsive to determining that a change between the identified subject and the one or more previously stored subject images and previously stored subject analyses exists ("Yes" branch, decision block 308), marker tracking program 110 updates subject analysis data (step 310). In one embodiment, marker tracking program 110 may update identified subject analysis data on a database, such as database 112. In another embodiment, marker tracking program 110 may update identified subject analysis data in a cloud-based environment over network 102 to be accessed by authorized users.

After storing the subject analysis data or following a determination that a relationship between the identified subject and the one or more previously stored images and the one or more previously stored subject analyses does not exist, marker tracking program 110 creates one or more subject analysis reports (step 312). A subject analysis report may include any relevant information pertaining to the one or more subjects represented in the report. A subject analyses report as used herein may be also be referenced as an object analysis report. In one embodiment, a subject analysis report may include the changes to the subject over time. For example, marker tracking program 110 may include data on the movement and growth of a subject, such as a tumor, in the body of a patient in the subject analysis report. In another example, marker tracking program 110 may include data on the shrinkage of a tumor in the body of a patient in a subject analysis report. In another embodiment, a subject analysis report may include suggested actions based on findings made by marker tracking program 110. For example, marker tracking program 110 may apply a machine learning algorithm, such as a supervised learning classifier, to suggest a medical exam with the highest probability of identifying one or more medical issues in a patient. Based on the information, marker tracking program 110 may include suggested medical exams in the subject analysis report to be displayed in a graphic user interface with interactive markers.

Marker tracking program 110 sends one or more subject analysis reports (step 314). In one embodiment, marker tracking program 110 may send the one or more subject analysis reports to one or more users, one or more data storage locations, one or more reports, one or more network destinations, and any combination thereof. For example, marker tracking program 110 may send a subject analysis report containing data regarding a tumor in the body of a patient to a primary care physician to provide a medical background. In another embodiment, marker tracking program 110 may send a subject analysis report to computing device 104. For example, marker tracking program 110 may send the subject analysis report to a desktop computer to be displayed passively next to one or more images. In another example, marker tracking program 110 may send the subject analysis report to a desktop computer to be displayed once marker tracking program 110 detects that a user selects a marker associated with the subject analysis report. In another example, marker tracking program 110 may send the one or more subject analysis reports to a centralized database in a cloud computing environment to be accessed my multiple users separately or in concert. However, marker tracking program 110 may send one or more subject analysis reports to any recipient and may send the one or more subject analyses in any manner and through any medium known in the art.

Figure 4:
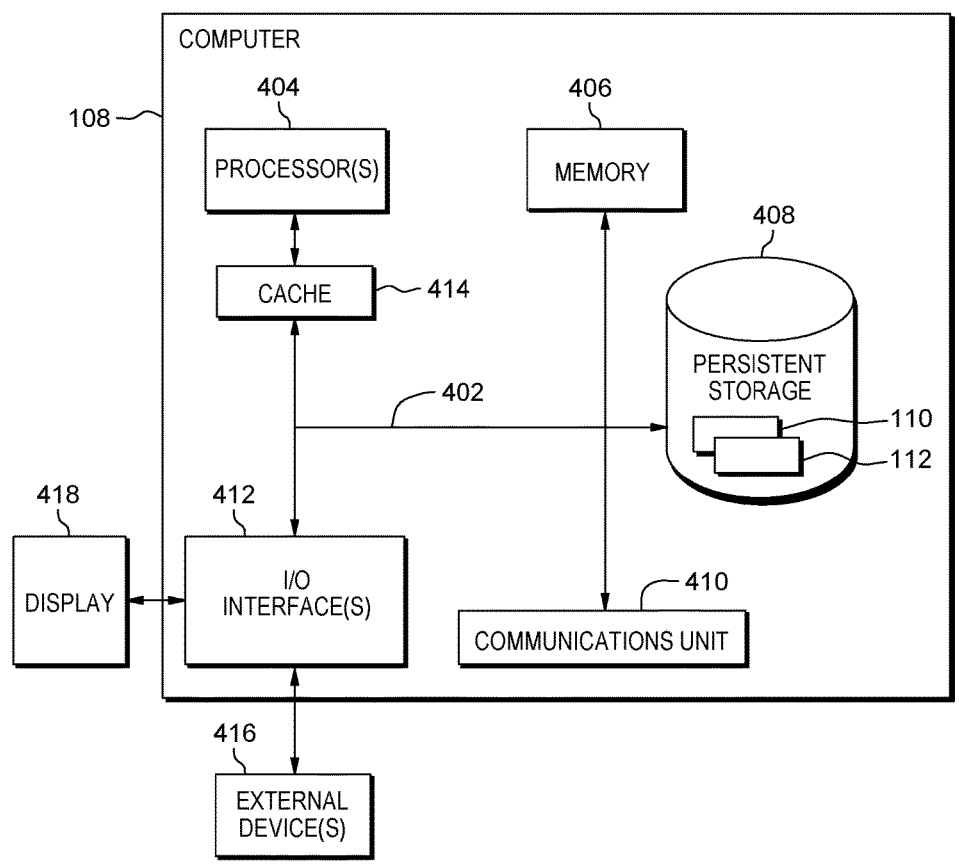
FIG. 4 depicts a block diagram of components of the server computer executing the marker tracking program within the distributed data processing environment of FIG. 1, in accordance with an embodiment of the present invention.

FIG. 4 depicts a block diagram of components of server computer 108 within distributed data processing environment 100 of FIG. 1, in accordance with an embodiment of the present invention. It should be appreciated that FIG. 4 provides only an illustration of one implementation and does not imply any limitations with regard to the environments in which different embodiments can be implemented. Many modifications to the depicted environment can be made.

Server computer 108 can include processor(s) 404, cache 414, memory 406, persistent storage 408, communications unit 410, input/output (I/O) interface(s) 412 and communications fabric 402. Communications fabric 402 provides communications between cache 414, memory 406, persistent storage 408, communications unit 410, and input/output (I/O) interface(s) 412. Communications fabric 402 can be implemented with any architecture designed for passing data and/or control information between processors (such as microprocessors, communications and network processors, etc.), system memory, peripheral devices, and any other hardware components within a system. For example, communications fabric 402 can be implemented with one or more buses.

Memory 406 and persistent storage 408 are computer readable storage media. In this embodiment, memory 406 includes random access memory (RAM). In general, memory 406 can include any suitable volatile or non-volatile computer readable storage media. Cache 414 is a fast memory that enhances the performance of processor(s) 404 by holding recently accessed data, and data near recently accessed data, from memory 406.

Program instructions and data used to practice embodiments of the present invention, e.g., marker tracking program 110 and database 112, are stored in persistent storage 408 for execution and/or access by one or more of the respective processor(s) 404 of server computer 108 via cache 414. In this embodiment, persistent storage 408 includes a magnetic hard disk drive. Alternatively, or in addition to a magnetic hard disk drive, persistent storage 408 can include a solid-state hard drive, a semiconductor storage device, a read-only memory (ROM), an erasable programmable read-only memory (EPROM), a flash memory, or any other computer readable storage media that is capable of storing program instructions or digital information.

The media used by persistent storage 408 may also be removable. For example, a removable hard drive may be used for persistent storage 408. Other examples include optical and magnetic disks, thumb drives, and smart cards that are inserted into a drive for transfer onto another computer readable storage medium that is also part of persistent storage 408.

Communications unit 410, in these examples, provides for communications with other data processing systems or devices, including resources of computing device 104. In these examples, communications unit 410 includes one or more network interface cards. Communications unit 410 may provide communications through the use of either or both physical and wireless communications links. Marker tracking program 110, database 112, and other programs and data used for implementation of the present invention, may be downloaded to persistent storage 408 of server computer 108 through communications unit 410.

I/O interface(s) 412 allows for input and output of data with other devices that may be connected to server computer 108. For example, I/O interface(s) 412 may provide a connection to external device(s) 416 such as a keyboard, a keypad, a touch screen, a microphone, a digital camera, and/or some other suitable input device. External device(s) 416 can also include portable computer readable storage media such as, for example, thumb drives, portable optical or magnetic disks, and memory cards. Software and data used to practice embodiments of the present invention, e.g., marker tracking program 110 and database 112 on server computer 108, can be stored on such portable computer readable storage media and can be loaded onto persistent storage 408 via I/O interface(s) 412. I/O interface(s) 412 also connect to a display 418.

Display 418 provides a mechanism to display data to a user and may be, for example, a computer monitor. Display 418 can also function as a touchscreen, such as a display of a tablet computer.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider.

The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 5:
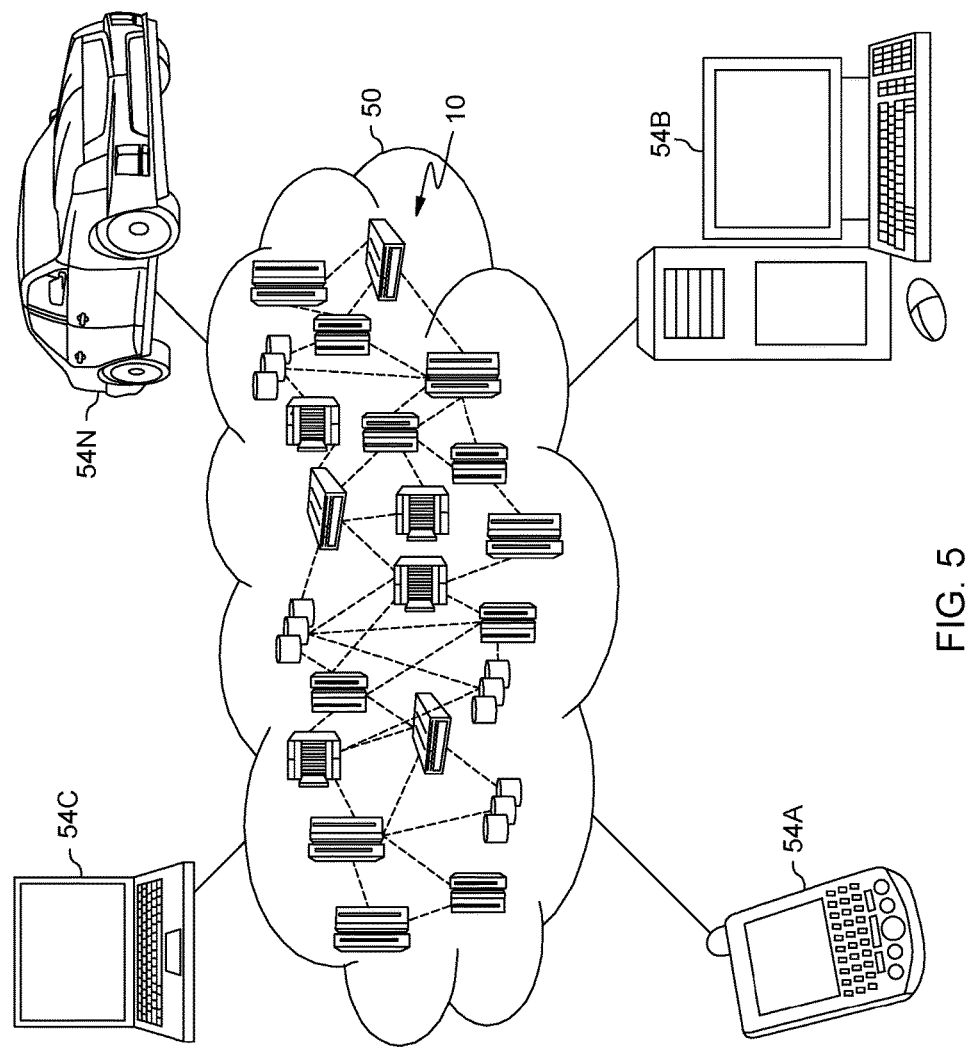
FIG. 5 depicts a cloud computing environment according to an embodiment of the present invention.

Referring now to FIG. 5, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. Server computer 108 may be one instance of node 10. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 1 are intended to be illustrative only and that computing nodes 10 and cloud computing environment 50 can communicate with any type of computerized device over any type of network and/or network addressable connection (e.g., using a web browser).

Figure 6:
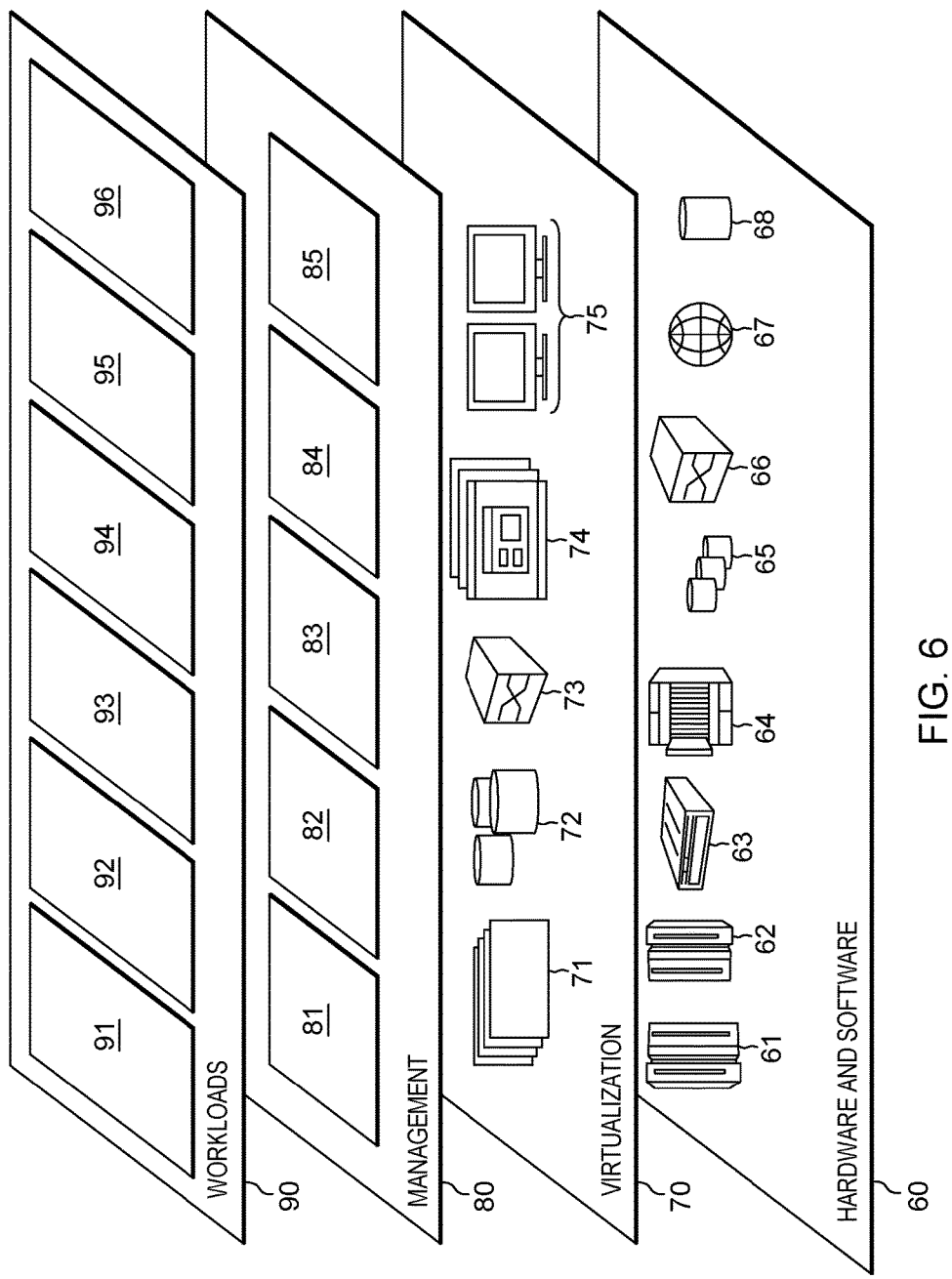
FIG. 6 depicts abstraction model layers according to an embodiment of the present invention.

Referring now to FIG. 6, a set of functional abstraction layers provided by cloud computing environment 50 (FIG. 1) is shown. It should be understood in advance that the components, layers, and functions shown in FIG. 7 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; lesion image processing 96; and marker tracking program 110.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A method for processing and displaying images, the method comprising:
    identifying, by one or more computer processors, one or more objects that exist in more than one image from a plurality of images, wherein the more than one image is more than one image of one or more lesions, and wherein identifying one or more objects that exist in more than one image from the plurality of images occurs based on prior data received from one or more users;
    analyzing, by the one or more computer processors, the identified one or more objects for one or more physical characteristics and one or more relationships between the identified one or more objects, wherein the one or more relationships between the one or more objects includes one or more temporal relationships, one or more spatial relationships, and one or more physical relationships;
    assigning, by the one or more computer processors, a marker to at least one object of the identified one or more objects on at least one image of the more than one image, wherein the marker is annotated based upon the one or more physical characteristics of the at least one object of the one or more identified objects, wherein the one or more physical characteristics of the identified one or more objects include size, shape, color, change in location, contrast, blurred, non-blurred, and opacities, wherein the annotation is based upon the one or more physical characteristics of the at least one object of the one or more identified objects is conveyed using a symbol, a color, alphanumeric text, and a size;

wherein assigning a marker to at least one object of the identified one or more objects on at least one image of the more than one image, wherein the marker is annotated based upon the one or more physical characteristics of the at least one object of the one or more identified objects further comprises:

identifying, by the one or more computer processors, a classification of the object based on the one or more physical characteristics of the at least one object of the one or more identified objects;

determining, by the one or more computer processors, the annotation associated with the one or more physical characteristics of the at least one object of the one or more identified objects;

associating, by the one or more computer processors, the marker with the determined annotation; and associating, by the one or more computer processors, the marker and the determined annotation with the object;

storing, by the one or more computer processors, the more than one images, analysis data, and marker data associated with the identified one or more objects and the marker;

manipulating, by the one or more computer processors, the one or more images based on a change in the one or more objects across the more than one image, wherein manipulating the one or more captured images is achieved by using manipulation techniques including a scaling, a centering, a rotation, an obliquity, a color, an opacity, and a transformation, wherein manipulating the one or more images based on a change in the one or more objects across the more than one image further comprises:

identifying, by the one or more computer processors, one or more unique physical traits of the one or more objects and one or more unique physical traits of the area surrounding the one or more objects in the more than one image;

analyzing, by the one or more computer processors, the one or more unique physical traits of the one or more objects and one or more unique physical traits of the area surrounding the one or more objects in the more than one image that are shared across the more than one image;

positioning, by the one or more computer processors, the one or more objects in the more than one image based on the shared one or more unique physical traits of the one or more objects and the shared one or more unique physical traits of the area surrounding the one or more objects in the more than one image in a first position; and adjusting, by the one or more computer, the first position of the one or more objects in the more than one image based on the differences between the one or more unique physical traits of the one or more objects and the differences between the one or more unique physical traits of the area surrounding the one or more objects in the more than one image in a second position;

receiving, by the one or more computer processors, the more than one image;

receiving, by the one or more computer processors, one or more analyses of the identified one or more objects;

creating, by the one or more computer processors, an image series from one or more stored images;

displaying, by the one or more computer processors, the one or more markers and the one or more analyses of the identified one or more objects and the one or more markers;

comparing, by the one or more computer processors, the one or more stored analyses data associated with the identified one or more objects to analysis data for at least one new image associated with the one or more objects;

determining, by the one or more computer processors, whether a difference between the one or more stored analyses data associated with the one or more objects and the analyses data for the at least one new image associated with the one or more objects exist; and responsive to determining that a difference exists between the one or more stored analyses associated with the one or more objects and the analysis data associated with the at least one new image associated with the one or more objects exists, creating, by the one or more computer processors, an object analysis report.

* * * * *